United States Patent

Blattberg

[11] Patent Number: 5,461,434
[45] Date of Patent: Oct. 24, 1995

[54] OPTICAL MEASUREMENT METHOD AND APPARATUS

[75] Inventor: Martin M. Blattberg, Brooklyn, N.Y.

[73] Assignee: MMB Optical, Brooklyn, N.Y.

[21] Appl. No.: 260,312

[22] Filed: Jun. 15, 1994

[51] Int. Cl.$^6$ .................................................. A61B 3/10
[52] U.S. Cl. ............................................ 351/204; 351/246
[58] Field of Search ............................ 351/200, 204, 351/246; 33/200

[56] References Cited

U.S. PATENT DOCUMENTS

| | | | |
|---|---|---|---|
| 2,361,534 | 10/1944 | Eppenstein | 88/20 |
| 2,477,518 | 7/1949 | Kappauf | 88/20 |
| 2,632,257 | 3/1953 | Belgard | 33/200 |
| 2,677,894 | 5/1954 | Belgard | 33/200 |
| 3,115,713 | 12/1963 | Johnston | 351/204 |
| 3,410,637 | 11/1968 | Jackson | 351/5 |
| 3,495,897 | 2/1970 | Deforges | 351/5 |
| 3,752,566 | 8/1973 | Mathews | 351/5 |
| 4,055,900 | 11/1977 | Grolman | 33/200 |
| 4,063,805 | 12/1977 | Gannon | 351/6 |
| 4,131,338 | 12/1978 | Zalewski | 351/5 |
| 4,160,330 | 7/1979 | Grolman | 33/200 |
| 4,167,067 | 9/1979 | Guiset | 33/200 |
| 4,196,978 | 4/1980 | Johnson | 351/5 |
| 4,252,419 | 2/1981 | Padula | 351/5 |
| 4,494,837 | 1/1985 | Bommarito | 351/204 |
| 4,531,297 | 7/1985 | Stoerr | 351/204 |
| 4,591,246 | 5/1986 | Cousyn | 351/204 |
| 4,653,192 | 3/1987 | Conrad et al. | 351/204 |
| 4,653,881 | 3/1987 | Joncour | 351/204 |
| 4,881,806 | 11/1989 | Bovet | 351/204 |
| 4,944,585 | 7/1990 | Mizuno | 351/204 |
| 4,988,185 | 1/1991 | Feinbloom | 351/233 |
| 5,033,840 | 7/1991 | Hennequin | 351/204 |
| 5,037,193 | 8/1991 | Funk | 351/204 |

Primary Examiner—William L. Sikes
Assistant Examiner—Huy Mai
Attorney, Agent, or Firm—Pollock, Vande Sande & Priddy

[57] ABSTRACT

A method and apparatus is described for interpupillary distance measurement. The device includes a frame and a pair of sliders. In use, the sliders are mounted in the frame and adjusted horizontally apart by the user and fixed in that position for later measurement. A bifocal or multifocal optical centering device and method is also described. The optical centering device includes a frame which is attached to a spectacle lens and a slider adjusted therein relative to the user's eye. The slider is then fixed for later measurement.

19 Claims, 2 Drawing Sheets

OPTICAL MEASUREMENT METHOD AND APPARATUS

FIELD OF THE INVENTION

The present invention relates to optical measurements in the field of vision correction, and more particularly to (a) measurement of interpupillary distance and (b) measurements useful for bifocal and multifocal optical centering.

BACKGROUND OF THE INVENTION

Over the years, many devices have been provided which are useful in the field of vision correction. Generally, the end result of the vision correction process is the production of a pair of spectacles for a user. The spectacles fit on the user's face, and include a spectacle frame. Within the spectacle frame are mounted left and right lenses which may provide for optical correction of the user's vision. The right lens provides the optical correction for the user's right eye (if necessary) and the left lens provides the correction for the user's left eye (if necessary).

Three pieces of information are essential for providing spectacles for the user which provide for effective vision correction. A first piece of information is a lens prescription. This piece of information defines the vision correction provided by the left and/or right lens. Two additional pieces of information are necessary for properly fitting vision correction. One of these is the interpupillary distance, i.e. the distance between the user's eyes. Finally, in the case where the user's optical correction includes a bifocal or multifocal lens, it is necessary to relate the optical center of the bifocal or multifocal lens with respect to the frame in which it is mounted. In this application, this relationship is termed bifocal segment placement (for a bifocal lens) or multifocal centering (for a multifocal lens), or generally as bifocal/multifocal centering.

Both the interpupillary distance and the bifocal/multifocal centering are specific to the user for whom the vision correction is intended.

Because vision-correction is important to a large segment of the population, there are service providers who make the measurements and, in some cases, provide spectacles in accordance with the measurements.

In some forms of spectacle-dispensing businesses, it would be useful if the interpupillary distance measurement and the bifocal/multifocal centering measurement could either be made by the user or indicated by the user. In some cases, this information will negate the requirement that the user physically visit the spectacle dispensary.

It is accordingly one object of the present invention to provide a device allowing a user to make or indicate the interpupillary distance measurement. It is another object of the present invention to provide a method by which a user can either make or indicate the interpupillary distance measurement. It is another object of the present invention to provide a device for assisting the user to make and/or indicate the bifocal/multifocal centering measurement. It is another object of the present invention to provide a method of allowing a user to make or assist in making the bifocal/multifocal centering measurement. To make or assist in the measurement, a bifocal/multifocal centering assist device is provided.

In accordance with one embodiment of the invention, a device for making or assisting in the making of the interpupillary distance measurement is provided. This device will be referred to as the interpupillary distance measurement assist. The interpupillary distance measurement assist in accordance with one form of the invention includes three major elements: a frame and a pair of slidable members. The frame includes a notch so that the frame can be conveniently supported on the nose of a user. The slidable members include a left slidable member and a right slidable member, each capable of being supported by the frame for horizontal movement relative to each other and relative to the frame. Each of the slidable members includes a small hole, sometimes referred to as a viewing hole, therein.

In use, the user places a viewing target on a convenient vertical surface at approximately eye level. The user then stands approximately 8–10 feet from the vertical surface supporting the viewing target and places the frame so that it is supported by the user's nose. The slidable members are moved relative to each other and relative to the frame so that the user can view the viewing target through each hole in the slidable member. At this point, the distance between the viewing holes is a measure of the user's interpupillary distance. With the frame and slidable members configured so that the user can view the viewing target through each hole, the slidable members are fixed relative to the frame. Thereafter, the user can remove the frame and easily measure the distance between the viewing holes. Alternatively, the frame and slidable members fixed relative thereto can be returned to a spectacle dispensary where the interpupillary distance can be readily measured.

As will be described hereinafter, the interpupillary measurement assist device can be manufactured for one-time use. The frame can be stamped or cut from a unitary piece of paper stock. As will be described hereinafter, the frame is generally rectangular but has an oval cut-out therein which will form a notch after the frame is properly assembled. The frame blank has first, second and third portions. Because the first, second and third portions of the frame are portions of a common rectangular blank, they all have a common length. The width of the first portion is reduced in part by the cutout which will form the notch. The second portion of the blank is directly adjacent the first portion and therefore has a cutout which is complementary to the cutout of the first portion. The first, second and third portions are then folded about first and second fold lines and secured by any convenient securing arrangement. Because the frame means comprises first, second and third portions, when properly folded, a pair of channels is formed, each for receiving one of the slidable members. This allows the slidable members to slide within a dedicated channel without interference from the other slidable member.

The slidable members are L-shaped and may be cut from the same paper stock. Each of the holes in the slidable member is formed in the base, as will be apparent from the drawings.

In accordance with another embodiment of the invention, the bifocal/multifocal centering measurement assist device is formed from paper stock so that it is disposable. Because the measurement designed to be revealed by the bifocal/multifocal centering device assist is related to the frame, the bifocal/multifocal centering device assist is designed to be used in conjunction with the spectacle frame chosen by the user. The bifocal/multifocal centering device assist includes a frame including a first pair of parallel legs separated by a second pair of parallel legs for defining a viewing window between the pairs of parallel legs. The bifocal/multifocal centering device assist also includes a convenient attachment for attaching the frame to a lens mounted in the spectacle frame. Typically, the lens will be a manufacturer's demonstration lens, i.e. the lens does not provide for vision correction. The attachment conveniently is adhesive-based. The bifocal/multifocal centering device assist also includes a slider having a slit therein. The slider has a length which is longer than one dimension of the frame and a width which is smaller than another dimension of the frame so that when the slider and frame are mated, in use, there is a vertically adjustable viewing position defined by the location of the slit portion of the slider within the viewing window defined by the frame.

In use, the user first positions a viewing target on a vertical surface at approximately eye level. The user then attaches the frame to a lens in the spectacle frame and places the spectacle frame in a normal using position supported on the user's face. The slider is placed between the horizontal legs of the frame and the lens to which it is secured so that the slit provides a viewing position at a vertically-adjustable location within the viewing window defined by the frame. The user then adjusts the vertical position of the slider so that the viewing target is centered in the visual area. At this point, the user can merely make the necessary measurement, measuring the vertical position of the slit relative to the frame. Typically, however, the user, rather than actually making the measurement, merely secures the slider to the frame and returns the entire combination, i.e. spectacle frame, frame and slider secured to the lens of the spectacle frame, to the dispensing business where the measurement can be made.

BRIEF DESCRIPTION OF THE DRAWINGS

The present invention will be described in further detail in the following portion of this specification when taken in conjunction with the attached drawings in which.

DETAILED DESCRIPTION OF PREFERRED EMBODIMENTS

Figure 1:
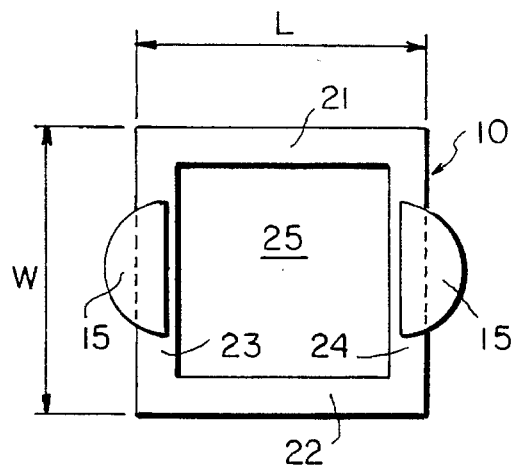
FIG. 1 is a front view of the frame and attachment elements of the bifocal/multifocal centering device assist.
Figure 2:
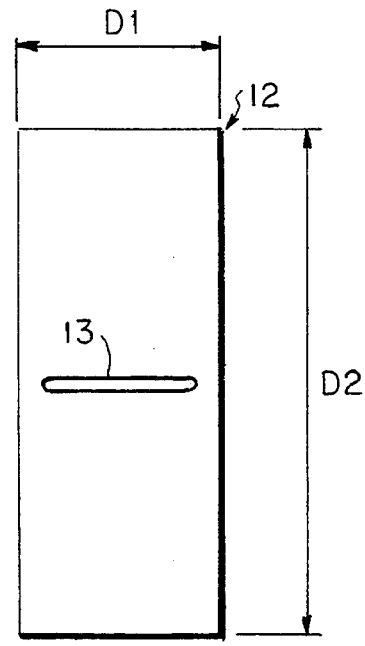
FIG. 2 is a front view of the slider portion of the bifocal/multifocal centering device assist.
Figure 3:
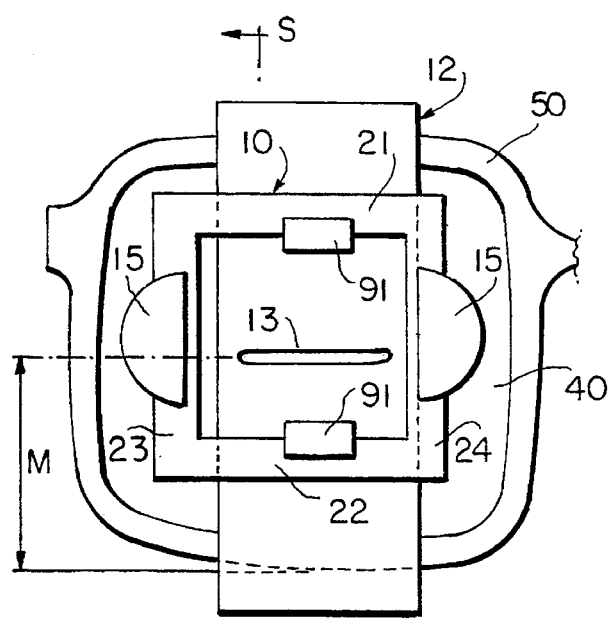
FIG. 3 is a front view of the assembled bifocal/multifocal centering device assist mounted on the lens of a spectacle frame.
Figure 4:
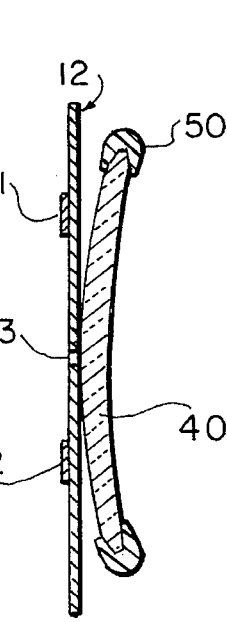
FIG. 4 is a cross-section of FIG. 3 showing the relationship between the lens, the slider and the frame.

FIGS. 1-4 illustrate the bifocal/multifocal centering device assist and show it in use. The device includes three major components: a frame 10, a slider 12, and a pair of adhesive tabs or attaching means 15. As shown in FIG. 1, the frame has a first pair of legs 21 and 22 of equal length and disposed generally parallel to each other. The frame includes a second pair of parallel legs 23 and 24, also disposed parallel to each other so as to define a viewing window 25. The frame itself can be formed by cutting from suitable paper stock. The length of the frame (indicated by the dimension L in FIG. 1) is selected to cover a substantial portion of a spectacle lens when the frame is located on the lens as shown in FIG. 3. Likewise, the other dimension of the frame, indicated by the reference character W in FIG. 1, is also chosen with the same criterion. The tabs 15 are any convenient adhesive-backed material (perhaps formed from the same paper stock as was the frame 10). The use for the tabs 15 will become apparent below. The second major component of the bifocal/multifocal centering device assist is the slider 12. The slider 12 has a first dimension D1 less than the dimension L of the frame 10. This allows the slider 12 to slide between the frame 10 and the lens to which it is attached, as is seen in FIGS. 3 and 4. The slider 12 has a second dimension D2 which is substantially larger than the dimension W so that when the slider 12 is positioned, the top or the bottom of the slider (or both) can be grasped by the user's fingers for movement relative to the spectacle lens and frame 10. The slider 12 includes a viewing slot 13. The dimension of the slot 13 parallel to the dimension D2 is small enough so that an accurate measurement can be made. Preferably the dimension parallel to the dimension D2 is approximately 0.15 mm. The other dimension of the slot (parallel to the dimension D1) should occupy a substantial portion of the slider 12 parallel to the dimension D1.

FIGS. 3 and 4 show the relationship of the bifocal/multifocal centering device assist and the spectacle frame 50 and lens 40 mounted therein. FIG. 3 is a section of FIG. 4 taken on the line SS. As is seen in FIGS. 3 and 4, the slider 12 is mounted between the lens 40 and the frame 10. As the slider 12 is moved vertically, the viewing position defined by the location of the slot 13 is varied.

In one embodiment of the invention which has been constructed, the frame has the following dimensions:

length L of the legs 21/22: 4.0 cm width of the legs 21/22: 0.5 cm length of the legs 23/24 :4.0 cm width of the legs 23/24: 0.5 cm the viewing window 25 is 3 cm×cm, the dimension D1 of the slider 12 is 3 cm, the dimension D2 of the slider 12 is 7 cm, the viewing the slit 13 has the dimensions 0.15 cm×2.2 cm.

the thickness of the paper stock forming the frame 10 and the slider 12 is about 0.015". In other embodiments, the thickness of the paper stock varied from 0.013" to about 0.020".

Figure 9:
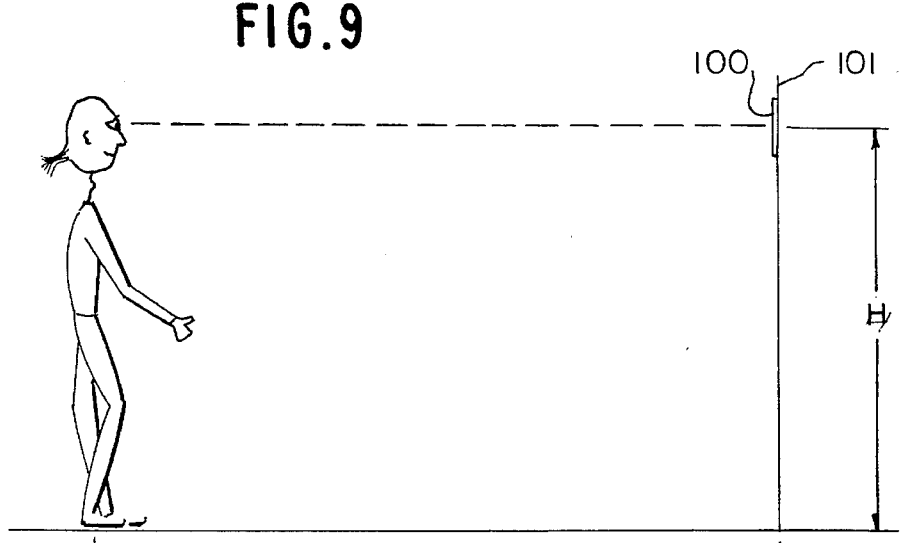
FIG. 9 schematically illustrates how the interpupillary device assist of FIGS. 5-8 and the bifocal/multifocal centering assist device of FIGS. 1-4 is put to actual use.

In use, the user first secures the frame 10 to the lens 40 mounted in the spectacle frame 50. The user then places a viewing target, such as the target 100 (see FIG. 9) on a suitable vertical surface 101. The viewing target 100 should be placed at a height H which is roughly equal to the user's eye level. The user then moves about 8–10 feet (the dimension D) from the vertical surface 10 and places the spectacle frame 50 in the normal using position. With one hand, the user covers the lens that does not have the bifocal/multifocal centering device assist located thereon. With the other eye (the one not covered by the user's hand), the user attempts to see the target while moving the slider 12 vertically until the target is centered in the visual area defined by the slit 13, while maintaining the user's head erect. The position of the slit 13, at this point in time, defines the desired bifocal/multifocal centering measurement. In order to preserve this measurement, the user can secure the slider 12 to the frame 10 by using an additional adhesive securing device such as the tabs 91 or any other suitable securing technique such as conventional adhesive tape. The bifocal/multifocal centering measurement is the distance noted M in FIG. 3. With the slider 12, and frame 10 secured to the lens 40, this measurement can be made by the user or a spectacle dispensary.

Figure 5:
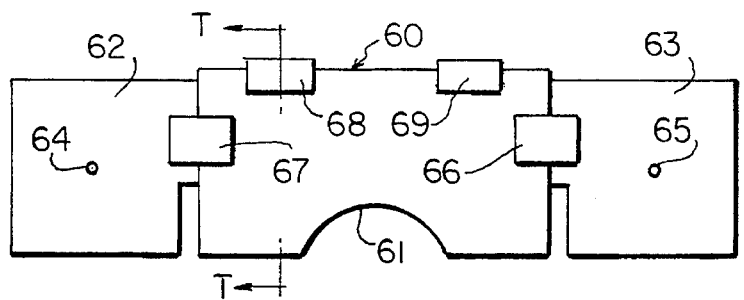
FIG. 5 is a front view of the interpupillary measurement device after it has been used so that the sliders are secured to the frame.
Figure 6:
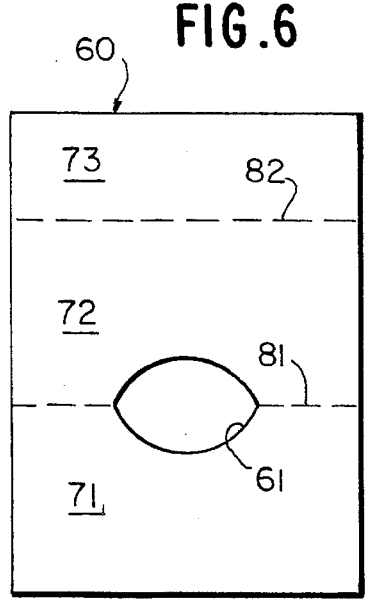
FIG. 6 shows the frame blank, after the cutout has been made but before it has been folded and assembled.
Figure 7:
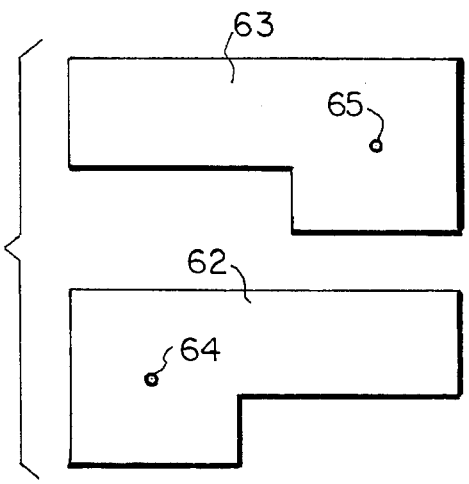
FIG. 7 is a front view of the two sliders.

Referring now to FIGS. 5–8, the interpupillary measurement assist device will be described. As seen in FIG. 5, the device includes three major components: a frame 60 having a notch 61, a left slider 62 and a right slider 63. As seen more clearly in FIG. 7, the sliders are each L-shaped, but complementary. The base of each leg of the slider has a viewing hole, 65 in the right slider and 64 in the left slider. The leg portions of the slider 62 and 63 ride in respective channels I and II of the frame (see FIG. 8).

Figure 8:
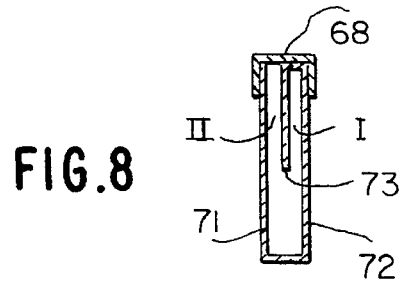
FIG. 8 is an end view of the frame after folding and assembly.

The frame is formed from a blank 160 (FIG. 6) which is generally rectangular in form except for the cutout which forms the notch 61. The frame 60 is formed by properly folding the blank along the fold lines 81 and 82 defining a first portion 71, a second portion 72 and a third portion 73. FIG. 8 is a section of the frame 60 along the line TT illustrating how, when the blank 160 is folded along the fold lines 81 and 82, the three portions 71–73 form a first channel I between the second portion 72 and the third portion 73, and a channel II between the first portion 71 and the third portion 73. The channels I and II each accepts one of the sliders 63 and 62 so that each of the sliders can move freely relative to each other and relative to the frame 60, in use. After having folded the blank 160 about the fold lines 81 and 82, the frame is secured in position by the securing elements 68 and 69. The elements 68 and 69 adhesively secure the frame in the folded form shown in Figs. 5 and 8. At this point, the sliders 62 and 63 can be inserted in their respective channels I and II. At this point, the interpupillary measurement assist device is ready for use.

In use (refer to FIG. 9), the user places a viewing target 100 on a suitable vertical surface 101 so that it is a distance H off the floor approximately equal to the user's eye level. The user then moves approximately 8–10 feet away (D) from the vertical surface 101. The interpupillary distance measurement assist device is then placed so that the notch 61 is supported on the user's nose. Then by moving the sliders 62 and 63 horizontally up and back, the user should be capable of seeing the viewing target simultaneously through both the holes 64 and 65. When the sliders are properly positioned, the user should see only one visual field with the viewing target centered therein. The adjustment of the sliders 62 and 63 is similar to adjusting binoculars for the proper interpupillary distance. When the sliders 62 and 63 are properly adjusted as noted above, then the interpupillary distance can be measured as the distance between the viewing holes 64 and 65. In order to preserve this distance, the sliders 62 and 63 are secured in position relative to the frame by the use of convenient adhesive stickers, adhesive tape or the like, such as the adhesive stickers 66 and 67 shown in FIG. 5. In this condition, the interpupillary distance can readily be measured as the distance between the holes 64 and 65. This measurement can be made either by the user or a spectacle dispensary.

In an embodiment of the invention which has been constructed, the blank 160 has the dimensions 6.5 cm×5 cm, the notch 61 is formed by an oval cutout, the distance between an edge of the blank 160 and the fold line 81 is 2.5 cm. The distance between the fold lines 81 and 82 is 2.5 cm and the distance between the fold line 82 and another edge of the blank 160 is 1.5 cm. Each of the movable sliders has a length 5.6 cm, the width of the leg is 1.6 cm and the width of the base is 2.4 cm. The viewing hole has a diameter of 0.15 cm. The blank 160 and the sliders 62 and 63 can be formed of suitable paper stock of thickness 0.015". In other embodiments, the thickness of the paper stock has varied from about 0.013" to about 0.020".

It should be apparent that while a preferred embodiment of the invention has been described, many changes can be made from the specific dimensions described herein within the spirit and scope of the invention. While in a preferred form the interpupillary measurement device assist and the bifocal/multifocal centering device assist are formed from paper stock, that is not essential to the invention and alternative materials are various forms of plastic and/or metal.

I claim:

1. A device for assisting in measurement of interpupillary distance comprising:

a) frame means including a locating notch for support on a nose of a user, b) a pair of slidable members, each with a small hole therein, a first slidable member with said hole near a left end thereof and a second slidable member with a small hole near a right end thereof, said frame means for supporting each said slidable member for movement relative to each other and relative to said frame means when said locating notch is located adjacent a nose of the user, whereby the interpupillary distance may be measured as the distance between the small holes of the slidable members.

2. A device as recited in claim 1 further including:

c) a first and second attachable retainer, each for retaining one of the slidable members in a fixed position relative to the frame means, whereby the interpupillary distance may be measured as the distance between the small holes when said slidable members are fixed in position by said first and second attachable retainers.

3. A device as recited in claim 1 wherein said frame means comprises first, second and third portions formed from a unitary piece of paper stock, said first portion having a generally rectangular form with length and width, with said notch therein reducing a width of said first portion to a lesser width, said second portion having a common edge with said first portion and of rectangular form with a length equal to the length of the first portion and a width less than the width of the first portion, said third portion substantially identical in form and size to the first portion and having a common edge with said first portion except in a region occupied by said notch, and at least one fastener securing said first and third portions relative to each other with the second portion lying between said first portion and the third portion to form a first and second channel, said first channel formed between the first and second portions and the second channel formed between the second portion and the third portion.

4. A device as recited in claim 3 wherein each said slidable member is L-shaped, with a first width extending over a portion of the length of the slidable member and a second, greater width, extending over the remainder of the length of the slidable member, said first width of the slidable member less than the lesser width of the first portion, said hole in each slidable member in that portion of the slidable member having said greater width.

5. A device as recited in claim 1 wherein said frame means includes first and second channels, each for receiving one of the slidable members for slidable movement therein, each slidable member being L-shaped with a first width extending over a portion of its length, said first width less than the width of each of said channels, each slidable member having a second, greater, width at one extremity with said small hole in the portion of the second, greater width.

6. A device as recited in claim 5 wherein said frame means and said slidable members are formed from paper stock.

7. A device as recited in claim 5 wherein said frame means is formed of a single piece of paper stock.

8. A kit for interpupillary measurement comprising the device as recited in claim 1 and a viewing target for wall mounting.

9. A method of interpupillary distance measurement comprising the steps of:

a) mounting a viewing target on a vertical surface at about eye level of a user, b) providing a frame with a pair of slidable members therein, each slidable member having a viewing hole therein, said frame having a notch for locating the frame adjacent the nose of the user, c) supporting the frame adjacent the nose of the user and moving the slidable members horizontally until the viewing target is visible to the user through each of the viewing holes, d) fixing the slidable members relative to the frame at the position reached in said step c), and e) measuring the interpupillary distance as the distance between the viewing holes in the slidable members.

10. A device for assisting in bifocal segment placement or multifocal centering comprising:

a) a frame defining a viewing window, b) attachment means for attaching said frame to a lens mounted in a spectacle frame, c) a generally rectangular slider with a slit therein, said slider having a length longer then the one dimension of the frame and a width smaller then a different dimension of the frame providing a vertically adjustable viewing position defined by the location of the slit within the viewing window, and d) securing means for securing the slider at one position relative to the frame when the frame is attached to the lens by the attachment means, whereby a bifocal segment placement or multifocal centering measurement is assisted by measuring the position of the slit of the slider relative to the spectacle frame when the slider is secured against movement relative to the frame.

11. A device as recited in claim 10 wherein: said frame has a first pair of parallel legs separated by a second pair of parallel legs for defining said viewing window therebetween.

12. A device as recited in claim 10 wherein the frame and slider are formed of paper stock.

13. A device as recited in claim 12 wherein said slit has a larger and a smaller dimension, said smaller dimension lying along the length of the slider and the larger dimension lying along the width of the slider.

14. A device as recited in claim 13 wherein the attachment means comprise adhesively backed members for attaching the frame to a lens mounted in a spectacle frame.

15. A device as recited in claim 14 wherein the securing means comprises one or more adhesive tabs for securing the slider in a fixed position relative to the frame.

16. A method of measuring a distance of assistance in bifocal or multifocal centering comprising the steps of:

a) providing a frame with a first pair of parallel legs separated by a second pair of parallel legs for defining a viewing window between the two pairs of legs, b) attaching said frame to a lens mounted in a spectacle frame, c) providing a generally rectangular slider with a slit therein, said slider having a length longer then the first pair of legs of the frame and a width smaller then the length of the second pair of legs of the frame providing a vertically adjustable viewing position defined by the location of the slit within the viewing window, d) mounting a viewing target on a vertical surface at substantially eye level of the user, e) placing the spectacle frame on the face of the user, f) locating the slider between the lens to which the frame is attached, and the frame, g) adjusting the vertical position of the slit by vertical movement of the slider relative to the viewing window until the viewing target is centered in a field of view of the user, and h) securing the slider relative to the frame at the position attained in said step g) to allow said distance to be measured by the position of the slit relative to the spectacle frame.

17. A method as recited in claim 16 wherein the user closes that eye which is not behind the frame.

18. A method as recited in claim 17 wherein the user blocks a field of view of that eye which is not behind the frame.

19. A kit for bifocal/multifocal centering measurement comprising the device recited in claim 10 and a viewing target for wall mounting.

* * * * *